United States Patent

Schaumann et al.

[11] Patent Number: 4,461,763
[45] Date of Patent: Jul. 24, 1984

[54] OXIMES OF 3'''-DEHYDROCARDENOLIDE TRIDIGITOXOSIDES

[75] Inventors: Wolfgang Schaumann, Heidelberg; Fritz Kaiser, Lampertheim; Wolfgang Voigtländer, Weinheim; Edgar Hoyer, Mannheim; Peter Neubert, Weinheim, all of Fed. Rep. of Germany

[73] Assignee: Boehringer Mannheim GmbH, Mannheim, Fed. Rep. of Germany

[21] Appl. No.: 439,654

[22] Filed: Nov. 5, 1982

[30] Foreign Application Priority Data

Nov. 26, 1981 [DE] Fed. Rep. of Germany ....... 3146898

[51] Int. Cl.³ .................. A61J 31/705; C07J 19/00
[52] U.S. Cl. ........................................ 424/182; 536/6.1
[58] Field of Search ...................... 536/6.1; 424/182

[56] References Cited

U.S. PATENT DOCUMENTS 3,981,862  7/1976  Voigtländer et al. ........... 536/6.1
4,021,546  5/1977  Bodor ................................ 536/6.1

FOREIGN PATENT DOCUMENTS 2343400  8/1973  Fed. Rep. of Germany ....... 536/6.1
7309305  7/1972  Netherlands ......................... 536/6.1

Primary Examiner—Donald B. Moyer
Assistant Examiner—C. Joseph Faraci
Attorney, Agent, or Firm—Felfe & Lynch

[57] ABSTRACT

The present invention provides 3'''-dehydrocardenolide tridigitoxoside oximes of the general formula:

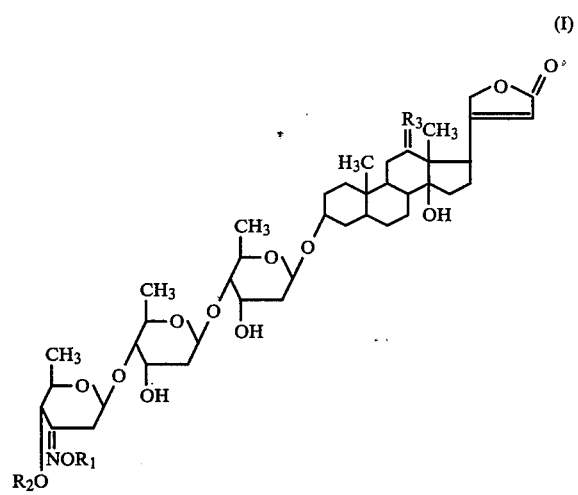

in which $R_1$ is a hydrogen atom or an alkyl radical containing up to 3 carbon atoms, $R_2$ is a hydrogen atom or a lower acyl or alkyl radical and $R_3$ represents two hydrogen atoms, the group

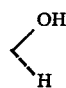

or the oximino group $=NOR_1$, wherein $R_1$ has the above-given meaning.

The present invention also provides a process for the preparation of these oximes, as well as pharmaceutical compositions containing them which are useful for the treatment of cardiac insufficiency.

19 Claims, No Drawings

OXIMES OF 3'''-DEHYDROCARDENOLIDE TRIDIGITOXOSIDES

The present invention is concerned with new oximes of 3'''-dehydrocardenolide tridigitoxosides, processes for the preparation thereof and pharmaceutical compositions containing them which are useful for the treatment of cardiac insufficiency.

The new oximes according to the present invention are compounds of the general formula:

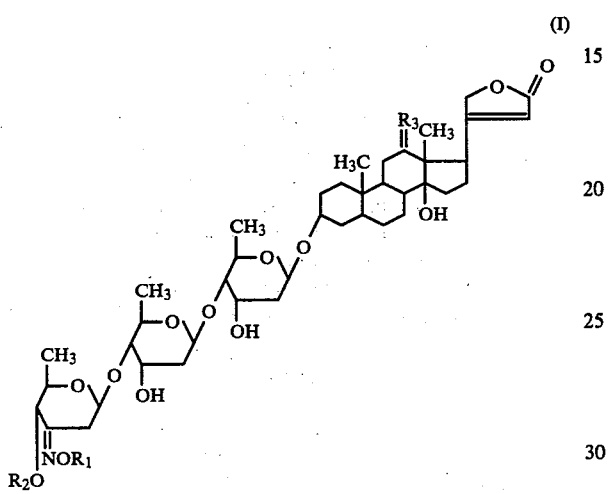

in which $R_1$ is a hydrogen atom or an alkyl radical containing up to 3 carbon atoms, $R_2$ is a hydrogen atom or a lower acyl or alkyl radical and $R_3$ represents two hydrogen atoms, the group

or the oximino group $=NOR_1$, wherein $R_1$ has the above-given meaning.

Acyl radicals are to be understood to be alkanoyl radicals containing up to 3 carbon atoms, the acetyl radical being preferred, and alkyl radicals are to be understood to contain up to 3 carbon atoms, the methyl radical being preferred.

The Digitalis glycosides digitoxin and digoxin mainly used in the therapy of heart insufficiency, together with derivatives thereof, for example acetyldigoxin and methyldigoxin, still leave something to be desired with regard to the safety of their use: digoxin and derivatives are preponderantly eliminated through the kidneys and can, therefore, give rise to intoxications in the case of patients with impaired kidney function. Digitoxin is the glycoside with the longest period of residence in the organism, for which reason possibly occurring intoxications, for example in the case of overdosing, can only subside again extremely slowly.

We have now found that the oximino derivatives of 3'''-dehydrocardenolide tridigitoxosides (I) according to the present invention assume an ideal middle position in that they are preponderantly eliminated extrarenally and thus are less dangerous in the case of impaired kidney function and, in addition, are eliminated considerably more quickly than digitoxin, the elimination times being similar to those of digoxin.

The new compounds of general formula (I) can be prepared by reacting a compound of the general formula:

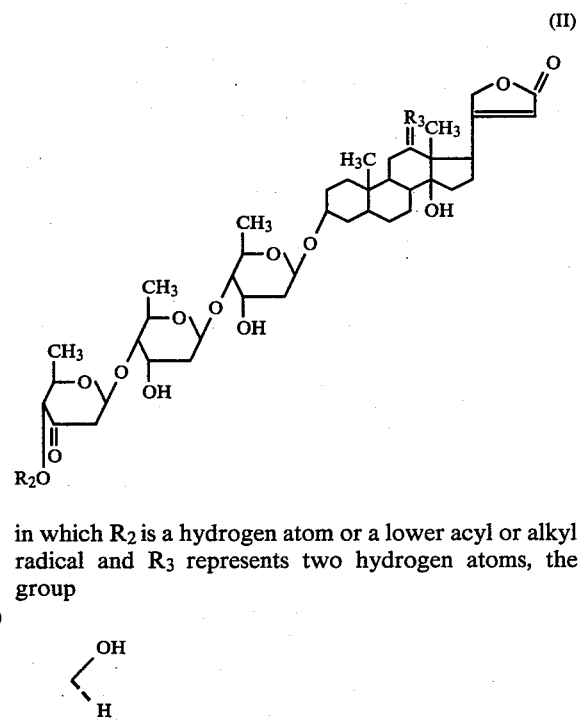

in which $R_2$ is a hydrogen atom or a lower acyl or alkyl radical and $R_3$ represents two hydrogen atoms, the group

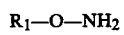

or an oxygen atom, in per se known manner with a hydroxylamine of the general formula:

$$R_1—O—NH_2 \qquad (III),$$

in which $R_1$ is a hydrogen atom or an alkyl radical containing up to 3 carbon atoms or with a salt thereof with an appropriate acid in a polar solvent, such as water, an alcohol, for example methanol, ethanol or isopropanol, a tert.-amine, such as pyridine or triethylamine, or dimethylformamide, at a temperature of from 20° C. up to the boiling point of the solvent, optionally with the addition of a base, such as a tert.-amine or an alkali metal hydroxide or carbonate.

The working up and purification of the end products is carried out in the usual way, for example by chromatographic processes or by multiplicative partitioning and crystallisation.

The identity and purity of the compounds obtained were examined by thin layer chromatography, using TLC finished plates (Merck silica gel 60/F 254, impregnation 20% formamide in acetone) and developing with the elution agent xylene-methyl ethyl ketone 2:3 v/v+5% formamide. The finished chromatograms were sprayed with trichloroacetic acid-chloramine reagent and the substances determined by their fluorescence in long wave UV ($\lambda=360$ nm). The running paths (R) in the chromatograms were, in each case, referred to a simultaneously run standard. $R_{Dt}$ thereby means the R value referred to the running path of 3'''-dehydrodigitoxin, $R_D$ the R value referred to the running path of 3''',12-didehydrodigoxin and $R_{Dg}$ the R value referred to the running path of 3'''-dehydrodigoxin.

The cardenolide glycosides according to the present invention can be administered 1 to 4 times daily in individual doses of 0.05–1.0 mg. Administration preferably takes place orally but a parenteral administration is also readily possible.

As the oral form of administration, tablets are preferred but hard capsules and soft gelatine capsules can also be used. For individual dosage administration, for example for children, the preparation can be in the form of a liquid. For emergency and in-patient treatment, administration can be carried out by the injection of appropriate solutions.

For the preparation of tablets or hard capsules for oral administration, the active material is homogeneously mixed with conventional adjuvants, such as lactose and starch but, because of the small individual doses, the production of a premixture is preferred. The active material-adjuvant material mixture can, by selection of appropriate adjuvants, be filled into hard capsules as a dry powder mass or, by granulation with binding agents, such as a starch slurry or polyvinylpyrrolidone, as a granulate or, after further admixture of appropriate breakdown agents and lubricants, can be pressed into tablets.

Carrier materials for soft gelatine capsules can be conventional glycerol fatty acid esters, as well as polyethyleneglycols as solvents for the active material. For a liquid or ampoule form, as solvents there can be used ethanol or polyhydroxy alcohols, optionally with the addition of water and other conventional adjuvants.

The advantages of the new compounds according to the present invention in comparison with digoxin and digitoxin, i.e. the combination of a rapid elimination with a high elimination rate via bile/faeces, are demonstrated by the following experimental protocol:

Experimental protocol

Groups of 4 cats each received an intravenous dose of 20 μg./kg. of one of the glycosides mentioned in the following Table. The glycosides were marked with tritium by the method of Haberland and Maerten as disclosed in German Published Specification No. 1959064 and digoxin was marked with tritium by the method of Wartburg as disclosed in Biochem Pharmacol, 14, 1883 (1965).

The radioactivity was determined in the urine and faeces portions collected separately after 2 and 7 days.

The values summarised in the Table give the elimination rate (column I) and the proportion of elimination in the urine (column II).

Column I indicates the amount eliminated in the urine and faeces after 2 days as a percentage of the total elimination after 7 days.

Column II indicates the percentage portion of the elimination in the urine after 7 days, referred to the total elimination in the urine and faeces after 7 days.

| glycoside | I | II |
|---|---|---|
| digoxin | 53 | 44 |
| digitoxin | 20 | 16 |
| 3'''-dehydrodigitoxin oxime | 53 | 14 |
| 3'''-dehydrodigitoxin methyloxime | 54 | 21 |
| 3'''-dehydrodigitoxin ethyloxime | 52 | 20 |
| 3''',12-didehydrodigoxin di-(methyloxime) | 45 | 21 |

The following Examples are given for the purpose of illustrating the present invention:

EXAMPLE 1

3'''-Dehydrodigitoxin oxime 2 g. 3'''-Dehydrodigitoxin are dissolved in 20 ml. pyridine and 40 ml. ethanol and, after the addition of 1 g. hydroxylamine hydrochloride, the reaction mixture is boiled under reflux for 1 hour, diluted with water and shaken out with chloroform. The chloroform phases are washed with 2N sulphuric acid, aqueous sodium carbonate solution and water, dried over anhydrous sodium sulphate and evaporated in a vacuum. The crude product obtained is crystallised twice from chloroform-methanol-diethyl ether to give 1.2 g. 3'''-dehydrodigitoxin oxime; m.p. 196°–199° C.; $R_{Di}$: 0.90.

EXAMPLE 2

3'''-Dehydrodigitoxin methyloxime 1 g. 3'''-Dehydrodigitoxin is dissolved in 20 ml. pyridine and, after the addition of 500 mg. O-methylhydroxylamine hydrochloride, the reaction mixture is left to stand for 1 day at ambient temperature and then worked up as described in Example 1. The crude product obtained is crystallised from acetone to give 870 mg. 3'''-dehydrodigitoxin methyloxime; m.p. 246°–249° C.; $R_{Di}$: 1.18.

EXAMPLE 3

3'''-Dehydrodigitoxin ethyloxime 1 g. 3'''-Dehydrodigitoxin is dissolved in 10 ml. pyridine and, after the addition of 500 mg. O-ethylhydroxylamine hydrochloride, the reaction mixture is left to stand for 3 days at ambient temperature, diluted with 100 ml. water, shaken out with chloroform and the chloroform phases, after washing with 2N sulphuric acid, aqueous sodium carbonate solution and water, dried over anhydrous sodium sulphate and evaporated in a vacuum. The crude product is separated with cyclohexane-ethyl acetate (3:1 v/v) over a cellulose column impregnated with formamide. The chromatographically uniform fractions give, after crystallisation from acetone, 450 mg. 3'''-dehydrodigitoxin ethyloxime; m.p. 261°–265° C.; $R_{Di}$: 1.28.

EXAMPLE 4

3''',12-Didehydrodigoxin dioxime 1 g. 3''',12-didehydrodigoxin is dissolved in 20 ml. pyridine and 20 ml. ethanol and, after the addition of 300 mg. hydroxylamine hydrochloride, the reaction mixture is boiled under reflux for 3 hours, worked up as described in Example 1 and the crude product, dissolved in chloroform-methanol (1:1 v/v) is mixed with animal charcoal, filtered over silica gel, evaporated and crystallised from acetone-diethyl ether to give 620 mg. 3''',12-didehydrodigoxin dioxime; m.p. 168°–172° C.; $R_D$: 0.69.

The 3''',12-didehydrodigoxin used as starting material is new and is prepared as follows:

10 g. Digoxin are dissolved in 400 ml. glacial acetic acid and mixed portionwise at ambient temperature within the course of 4 hours with 160 ml. 2% chromium trioxide-glacial acetic acid solution. Subsequently, the reaction mixture is diluted with 1.5 liters of chloroform, washed twice with 250 ml. amounts of 2N sulphuric acid and twice with 250 ml. amounts of water, dried over anhydrous sodium sulphate and evaporated in a vacuum. The crude product is fractionated over silica gel with chloroform+2% methanol. The chromatographically uniform fractions yield, after crystallisation from chloroform-diethyl ether, 6.5 g. 3'''-didehydrodigoxin; m.p. 206°–210° C.

EXAMPLE 5

3''',12-Didehydrodigoxin di-(methyloxime)

1 g. 3''',12-Didehydrodigoxin is dissolved in 20 ml. pyridine and 20 ml. ethanol and, after the addition of 500 mg. O-methylhydroxylamine hydrochloride, is reacted and worked up as described in Example 4. The crude product is separated with cyclohexane-ethyl acetate (2:1 v/v) over a cellulose column impregnated with formamide. The chromatographically uniform fractions yield, after crystallisation from acetone-diethyl ether, 450 mg. 3''',12-didehydrodigoxin di-(methyloxide); m.p. 239°–243° C.; $R_D$: 1.35.

EXAMPLE 6

3'''12-Didehydrodigoxin di-(ethyloxime)

1 g. 3''',12-Didehydrodigoxin is dissolved in 10 ml. pyridine and, after the addition of 500 mg. O-ethylhydroxylamine hydrochloride, the reaction mixture is left to stand for 3 days at ambient temperature and worked up as described in Example 3. The crude product is separated with heptane-methyl ethyl ketone (3:1 v/v) over a cellulose column impregnated with formamide. The chromatographically uniform fractions yield, after crystallisation from acetone, 430 mg. 3''',12-didehydrodigoxin di-(ethyloxime); m.p. 241°–245° C.; $R_D$: 1.43.

EXAMPLE 7

3'''-Dehydrodigoxin methyloxime 1 g. 3'''-Dehydrodigoxin is dissolved in 20 ml. pyridine and, after the addition of 120 mg. O-methylhydroxylamine hydrochloride, the reaction mixture is left to stand for 30 minutes at ambient temperature and worked up as described in Example 1. The crude product is crystallised from acetone to give 820 mg. 3'''-dehydrodigoxin methyloxime; m.p. 251°–254° C.; $R_{Dg}$: 1.43.

EXAMPLE 8

4'''-Acetyl-3'''-dehydrodigitoxin oxime 2 g. 3'''-Dehydrodigitoxin oxime are dissolved in 20 ml. dimethylformamide and, after the addition of 400 mg. triethylenediamine and 0.26 ml. acetic anhydride, left to stand for 20 hours at ambient temperature. The reaction mixture is then diluted with 150 ml. water, shaken out with chloroform and the chloroform phases are evaporated in a vacuum. The crude product is separated with cyclohexane-ethyl acetate (3:1 v/v) over a cellulose column impregnated with formamide. The chromatographically uniform fractions give, after crystallisation from ethyl acetate, 620 mg. 4'''-acetyl-3'''-dehydrodigitoxin oxime; m.p. 202°–205° C.; $R_D$: 1.09.

EXAMPLE 9

4'''-Acetyl-3'''-dehydrodigitoxin methyloxime 2 g. 3'''-Dehydrodigitoxin methyloxime are dissolved in 20 ml. dimethylformamide and, after the addition of 400 mg. triethylenediamine and 0.26 ml. acetic anhydride, reacted and worked up as described in Example 8. The crude product is separated with heptane-methyl ethyl ketone (2:1 v/v) over a cellulose column impregnated with formamide. The chromatographically uniform fractions give, after crystallisation from acetone, 1.2 g. 4'''-acetyl-3'''-dehydrodigitoxin methyloxime; m.p. 233°–236° C.; $R_D$: 1.32.

EXAMPLE 10

4'''-Methyl-3'''-dehydrodigitoxin oxime 1.8 g. 4'''-Methyl-3'''-dehydrodigitoxin are dissolved in 72 ml. pyridine and, after the addition of 720 mg. hydroxylamine hydrochloride, heated to 100° C. for 2 hours, then diluted with 900 ml. water, shaken out with chloroform and the chloroform phases are washed with water, dried over anhydrous sodium sulphate and evaporated in a vacuum. The crude product is separated with cyclohexane-ethyl acetate (2:1 v/v) over a cellulose column impregnated with formamide. The chromatographically uniform fractions yield, after crystallisation from acetone-diethyl ether, 1.05 g. 4'''-methyl-3'''-dehydrodigitoxin oxime; m.p. 193°–195° C.; $R_D$: 1.11.

The 4'''-methyl-3'''-dehydrodigitoxin used as starting material is new and is prepared in the following manner:

6 g. Chromium trioxide are introduced at ambient temperature, while stirring, into a mixture of 8 ml. pyridine and 150 ml. methylene chloride and stirred for 15 minutes at ambient temperature. A solution of 8 g. 4'''-methyldigitoxin in 10 ml. pyridine and 100 ml. methylene chloride is slowly added thereto. The reaction mixture is stirred for 15 minutes at ambient temperature, boiled under reflux for 1 hour, diluted with 500 ml. water, shaken out with chloroform and the chloroform phases are washed with a 5% aqueous solution of sodium bicarbonate and with water, dried over anhydrous sodium sulphate and evaporated in a vacuum. The crude product is separated with heptane-methyl ethyl ketone (2:1 v/v) over a cellulose column impregnated with formamide. The chromatographically uniform fractions yield, after crystallisation from chloroform-diethyl ether, 4.2 g. 4'''-methyl-3'''-dehydrodigitoxin; m.p. 213°–217° C.

EXAMPLE 11

4'''-Methyl-3'''-dehydrodigitoxin methyloxime 1 g. 4'''-Methyl-3'''-dehydrodigitoxin is dissolved in 5 ml. pyridine and, after the addition of 250 mg. O-methylhydroxylamine hydrochloride, reacted and worked up as described in Example 2. The crude product is crystallised from methanol-water (5:2 v/v) and yields 720 mg. 4'''-methyl-3'''-dehydrodigitoxin methyloxime; m.p. 171°–175° C.; $R_D$: 1.36.

EXAMPLE 12

4'''-Methyl-3'''-dehydrodigoxin oxime 1 g. 4'''-Methyl-3'''-dehydrodigoxin is dissolved in 10 ml. pyridine and 20 ml. ethanol and, after the addition of 500 mg. hydroxylamine hydrochloride, reacted and worked up as described in Example 1. The crude product gives, after crystallisation from ethyl acetate-diethyl ether, 680 mg. 4'''-methyl-3'''-dehydrodigoxin oxime; m.p. 159°–163° C.; $R_{Dg}$: 1.74.

EXAMPLE 13

4'''-Acetyl-3''',12-didehydrodigoxin di-(methyloxime)

1 g. 3''',12-Didehydrodigoxin di-(methyloxime) is dissolved in 10 ml. dimethylformamide and, after the addition of 200 mg. triethylenediamine and 0.20 ml.

acetic anhydride, reacted and worked up as described in Example 8. The crude product is separated with cyclohexane-ethyl acetate (4:1 v/v) over a cellulose column impregnated with formamide. The chromatographically uniform fractions yield, after crystallisation from diethyl ether-petroleum ether, 490 mg. 4'''-acetyl-3''',12-didehydrodigoxin di-(methyloxime); m.p. 126°–130° C.; $R_D$: 1.86.

EXAMPLE 14

4'''-Methyl-3''',12-didehydrodigoxin dioxime 1 g. 4'''-Methyl-3''',12-didehydrodigoxin is dissolved in 20 ml. pyridine and 20 ml. ethanol and, after the addition of 300 mg. hydroxylamine hydrochloride, boiled under reflux for 3 hours and then worked up in the manner described in Example 1. The crude product yields, after crystallisation from methanol-water, 630 mg. 4'''-methyl-3''',12-dehydrodigoxin dioxime; m.p. 154°–158° C.; $R_D$: 1.13.

The 4'''-methyl-3''',12-didehydrodigoxin used as starting material is new and is prepared in the following manner:

10 g. 4'''-Methyldigoxin are dissolved in 400 ml. glacial acetic acid and mixed portionwise at ambient temperature in the course of 4 hours with 160 ml. 2% chromium trioxide glacial acetic acid solution. The reaction mixture is subsequently diluted with 1.5 liters chloroform, washed twice with 250 ml. amounts of 2N sulphuric acid and twice with 250 ml. amounts of water, dried over anhydrous sodium sulphate and evaporated in a vacuum. The crude product is fractionated with chloroform+1% methanol over silica gel. The chromatographically uniform fractions yield, after crystallisation from chloroform-methanol-diethyl ether, 5.9 g. 4'''-methyl-3''',12-didehydrodigoxin; m.p. 209°–212° C.

EXAMPLE 15

4'''-Methyl-3''',12-didehydrodigoxin di-(methyloxime)

1 g. 4'''-Methyl-3''',12-didehydrodigoxin is dissolved in 20 ml. pyridine and 20 ml. ethanol and, after the addition of 500 mg. O-methylhydroxylamine hydrochloride, reacted and worked up as described in Example 14. The crude product yields, after crystallisation from acetone-diethyl ether-petroleum ether, 520 mg. 4'''-methyl-3''',12-didehydrodigoxin di-(methyloxime); m.p. 89°–93° C.; $R_D$: 1.87.

It will be understood that the specification and examples are illustrative but not limitative of the present invention and that other embodiments within the spirit and scope of the invention will suggest themselves to those skilled in the art.

What is claimed is:

1. A 3'''-dehydrocardenolide tridigitoxoside oxime selected from the group consisting of compounds of the formula:

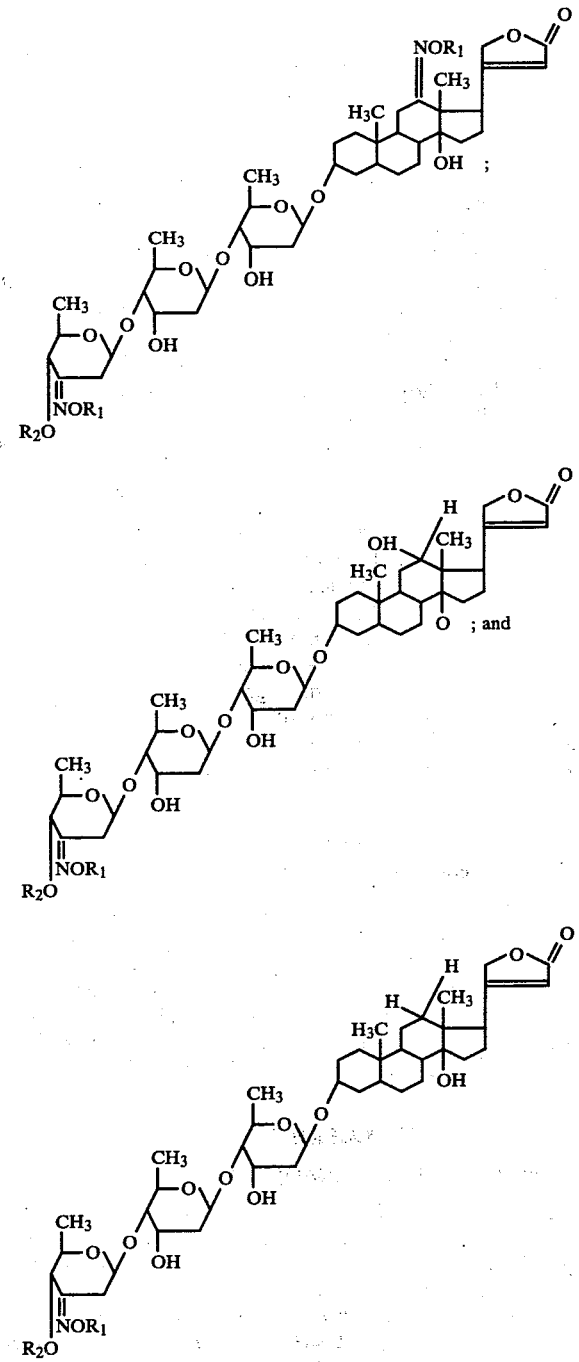

in which $R_1$ is a hydrogen or an alkyl radical containing up to 3 carbon atoms, and $R_2$ is a hydrogen atom or a lower carboxylic acyl or alkyl radical of up to 3 carbon atoms.

2. The oxime of claim 1 wherein $R_1$ is a hydrogen atom.

3. The oxime of claim 1 wherein $R_1$ is an alkyl of up to 3 carbon atoms.

4. The oxime of claim 1 wherein $R_2$ is a hydrogen atom.

5. The oxime of claim 1 wherein $R_2$ is lower acyl.

6. The oxime of claim 1 wherein $R_2$ is an alkyl radical of up to 3 carbons.

7. The oxime of claim 1 having the formula

8. The oxime of claim 1 having the formula

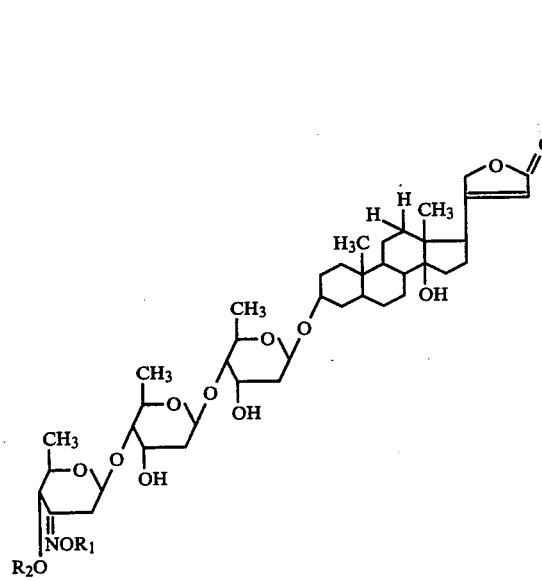

9. The oxime of claim 1 having the formula

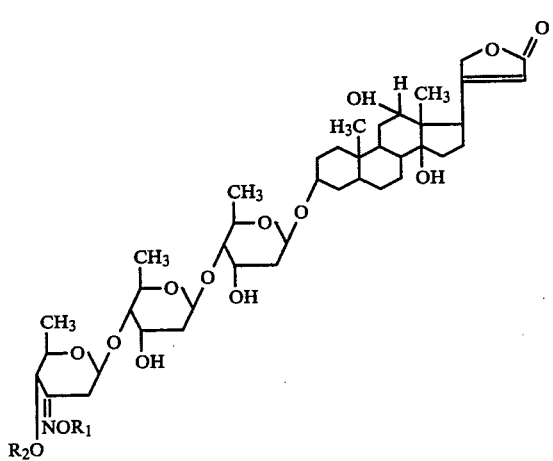

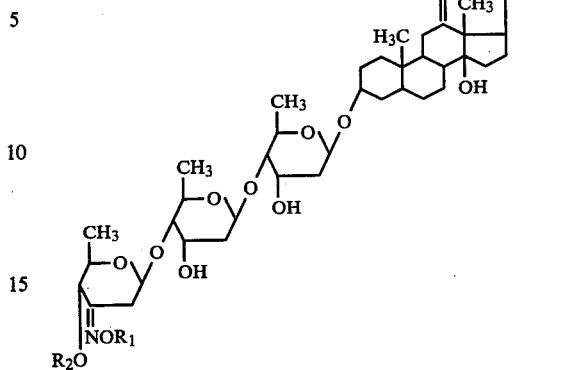

10. The oxime of claim 1 wherein $R_2$ is acetyl.

11. The oxime of claim 1 wherein $R_2$ is methyl.

12. The oxime of claim 1 selected from the group consisting of 3'''-dehydrodigitoxin oxime, 3'''-dehydrodigitoxin methyloxime and 3'''-dehydrodigitoxin ethyloxime.

13. The oxime of claim 1 selected from the group consisting of 3''',12-dehydrodigoxin dioxime, 3''',12-dehydrodigoxin di-(methyloxime) and 3''',12-didehydrodigoxin di-(ethyloxime).

14. The oxime of claim 1 which is designated 3''' dehydrodigoxin methyloxime.

15. The oxime of claim 1 selected from the group consisting of 4'''-methyl-3'''-dehydrodigitoxine oxime, 4'''-methyl-3'''-dehydrodigitoxin methyloxime and 4'''-methyl-3'''-dehydrodigoxin oxime.

16. The oxime of claim 1 selected from the group consisting of 4'''-methyl-3''',12-didehydrodigoxin di-(methyloxime), 4'''-methyl-3''',12-didehydrodigoxin dioxime, and 4'''-methyl-3''',12-didehydrodigoxin di-(methyloxime).

17. Pharmaceutical composition for treating cardiac insufficiency consisting of a cadiotonic effective amount of at least one oxime according to claim 1, in admixture with a pharmaceutical diluent or carrier.

18. A method of treating a cardiac insufficiency in mammals, which comprises administering a cardioactive effective amount of a compound according to claim 1.

19. The oxime of claim 1 selected from the group consisting of
4'''-acetyl-3'''-dehydrodigitoxin oxime and
4'''-acetyl-3'''-dehydrodigitoxin methyloxime.

* * * * *